(12) United States Patent
Troller et al.

(10) Patent No.: US 11,266,302 B2
(45) Date of Patent: Mar. 8, 2022

(54) MICRO-ENDOSCOPE AND METHOD OF MAKING SAME

(71) Applicant: Clear Image Technology, LLC, Elyria, OH (US)

(72) Inventors: Stefan Troller, Sissach (CH); Urban Schnell, Munchenbuchsee (CH); Matthias Pfister, Bern (CH); Michel Saint-Ghislain, Dudingen (CH)

(73) Assignee: Clear Image Technology, LLC, Elyria, OH (US)

( * ) Notice: Subject to any disclaimer, the term of this patent is extended or adjusted under 35 U.S.C. 154(b) by 428 days.

(21) Appl. No.: 16/265,829

(22) Filed: Feb. 1, 2019

(65) Prior Publication Data

US 2019/0167073 A1   Jun. 6, 2019

Related U.S. Application Data

(62) Division of application No. 14/826,255, filed on Aug. 14, 2015, now Pat. No. 10,973,393.

(60) Provisional application No. 62/039,518, filed on Aug. 20, 2014.

(51) Int. Cl.
| | |
|---|---|
| *A61B 1/00* | (2006.01) |
| *A61B 1/07* | (2006.01) |
| *A61B 1/06* | (2006.01) |
| *A61B 1/05* | (2006.01) |

(52) U.S. Cl.
CPC ............ *A61B 1/0011* (2013.01); *A61B 1/051* (2013.01); *A61B 1/0607* (2013.01); *A61B 1/07* (2013.01)

(58) Field of Classification Search
CPC ......... A61B 1/0011; A61B 1/051; A61B 1/07; A61B 1/0607
See application file for complete search history.

(56) References Cited

U.S. PATENT DOCUMENTS

| | | | | |
|---|---|---|---|---|
| 6,124,883 | A * | 9/2000 | Suzuki | A61B 1/00165 348/68 |
| 2003/0179448 | A1* | 9/2003 | Ramsbottom | G02B 23/26 359/435 |
| 2004/0064018 | A1* | 4/2004 | Dunki-Jacobs | A61B 1/07 600/178 |
| 2007/0191684 | A1* | 8/2007 | Hirata | A61B 1/0676 600/179 |
| 2008/0045802 | A1* | 2/2008 | Brandstaetter | A61B 1/0607 600/199 |
| 2009/0190371 | A1* | 7/2009 | Root | G02B 6/0006 362/554 |
| 2013/0155719 | A1* | 6/2013 | Bratt | F21K 9/61 362/609 |
| 2014/0336457 | A1* | 11/2014 | Kuhn | G02B 23/2423 600/109 |

\* cited by examiner

*Primary Examiner* — Timothy J Neal
*Assistant Examiner* — Genja M Frankert
(74) *Attorney, Agent, or Firm* — Law Office of Scott C Harris, Inc; Scott C Harris

(57) ABSTRACT

A micro-endoscope and method of making the same includes a mounting housing, a camera module received within the mounting housing, and an encapsulation material interposed between the camera module and the mounting housing for fixedly mounting the camera module within the mounting housing and/or inhibiting the passage of light between the camera module and the mounting housing. The micro-endoscope further includes a light guide having the mounting housing received therein.

7 Claims, 4 Drawing Sheets

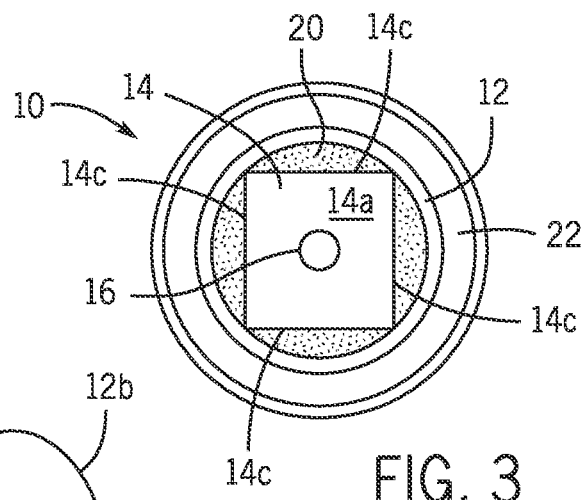
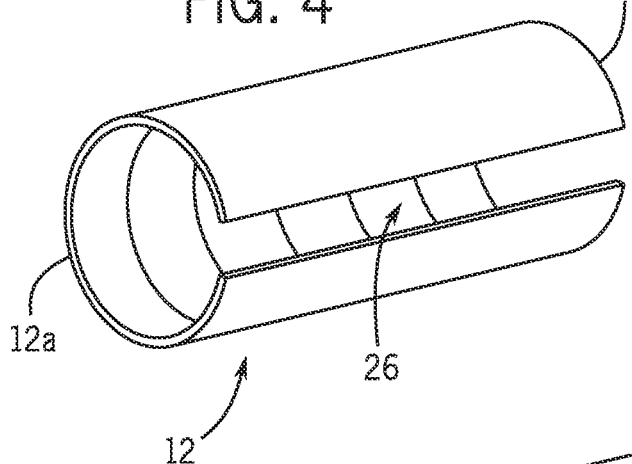
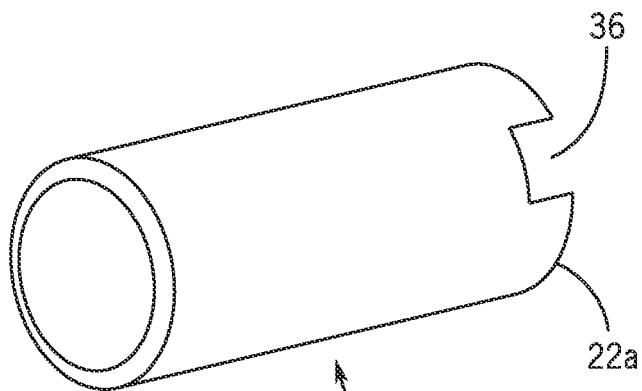
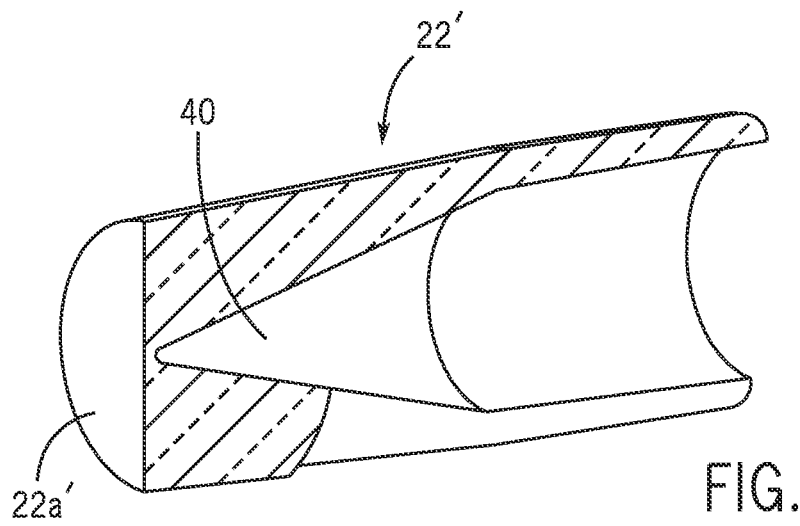

MICRO-ENDOSCOPE AND METHOD OF MAKING SAME

The present application claims priority to U.S. Prov. App. Ser. No. 62/039,518, filed Aug. 20, 2014, the entity of which is expressly incorporated herein by reference.

BACKGROUND

The present disclosure generally relates to medical devices, and more particularly relates to a micro-endoscope and a method of making the same. Micro-endoscopes are a type of endoscope having a very small cross-sectional dimension. This can present unique manufacturing challenges for the micro-endoscope. By way of example, a micro-endoscope can have an outside diameter that is less than about 4.0 mm. This small size inhibits easy manufacture of the micro-endoscope and makes it difficult to position an image capturing device, such as a camera, near the distal end of the micro-endoscope.

In one known micro-endoscope, a camera module is painted with a black paint and installed within an optical light guide near the distal end of the micro-endoscope. In particular, lateral sides of the camera module are painted with a thin coat of black paint and the camera module is fit via an interference fit within the light guide. Then, both the camera module and the light guide are received with in a steel outer sheath.

There are a number of potential drawbacks with this arrangement. For example, the dimensions of the camera module alone and/or the camera module with the black paint thereon can be too inconsistent resulting in problems when inserting the camera in the light guide tube. Also, the attachment of a ribbon cable to the back of the camera module can be susceptible to failure due to the connection being maintained by only relatively weak solder connections. Additionally, the micro-endoscope can suffer from decreased optical output due to stray light passing by the camera module. Further, the black paint can sometimes interfere with the optics of the camera module and it is possible for parasitic paint particles to develop due to local detachment of the black paint.

SUMMARY

According to one aspect, a micro-endoscope device for insertion into a body includes a camera module received within a mounting tube and an encapsulation material interposed between the camera module and the mounting tube. The micro-endoscope device further includes a light guide tube annularly disposed around the mounting tube for transmitting light axially past the camera module and the mounting tube.

According to another aspect, a micro-endoscope with an encapsulated camera includes a mounting housing, a camera module received within the mounting housing, and an encapsulation material interposed between the camera module and the mounting housing for fixedly mounting the camera module within the mounting housing and/or inhibiting the passage of light between the camera module and the mounting housing. The micro-endoscope further includes a light guide having the mounting housing received therein.

According to a further aspect, a method of making a micro-endoscope includes inserting a camera module into a mounting housing and at least partially encapsulating the camera module with an encapsulation material interposed between the camera module and the mounting housing for fixedly mounting the camera module within the mounting housing and/or inhibiting the passage of light between the camera module and the mounting housing. The method further includes inserting the mounting housing into a light guide tube.

BRIEF DESCRIPTION OF THE DRAWINGS

FIG. 3 is a front elevation view of the micro-endoscope of FIG. 1.

FIG. 4 is an isolated perspective view of a mounting tube of the micro-endoscope of FIG. 1.

FIG. 5 is an isolated perspective view of a light guide tube of the micro-endoscope of FIG. 1.

FIG. 6 is an isolated perspective view of a light guide tube according to an alternate exemplary embodiment.

DETAILED DESCRIPTION

Figure 1:
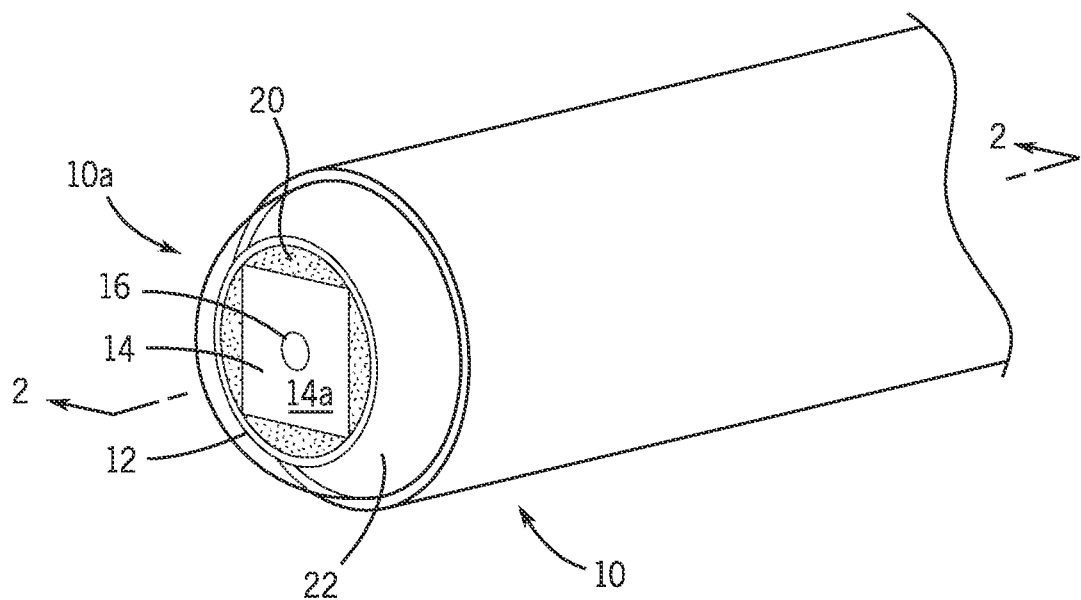
FIG. 1 is a partial perspective view of a micro-endoscope with an encapsulated camera according to an exemplary embodiment.

Referring now to the drawings wherein the showings are for purposes of illustrating one or more exemplary embodiments and not for purposes of limiting the same, FIG. 1 illustrates a micro-device adapted for insertion into a body (e.g., a human body) and generally designated by reference 10. As also described in more detail herein, the micro-device 10 is a micro-endoscope with an encapsulated camera in the illustrated embodiment. The micro-endoscope 10 can be part of an endoscope system (e.g., an arthroscopic system or some other scope system) that additionally includes a reusable hand piece, a display/console, appropriate software and image enhancement algorithms, etc. (none of foregoing are shown in the illustrated embodiment). In one configuration, the micro-endoscope 10 can be provided in a package for use as a single-use item (i.e., the micro-endoscope 10 can be a disposable endoscope designed for single use). By way of example, the outside diameter of the illustrated micro-endoscope can be less than 3 mm, preferably less than 2.5 mm, and more preferably approximately 2.2 mm, though other dimensions could be used. In the illustrated embodiment, the cross-section of the micro-endoscope is circular or round but this is not required (e.g., the micro-endoscope 10 could have a oval cross-section, rectangular cross-section, octagonal cross-section, etc.).

Figure 2:
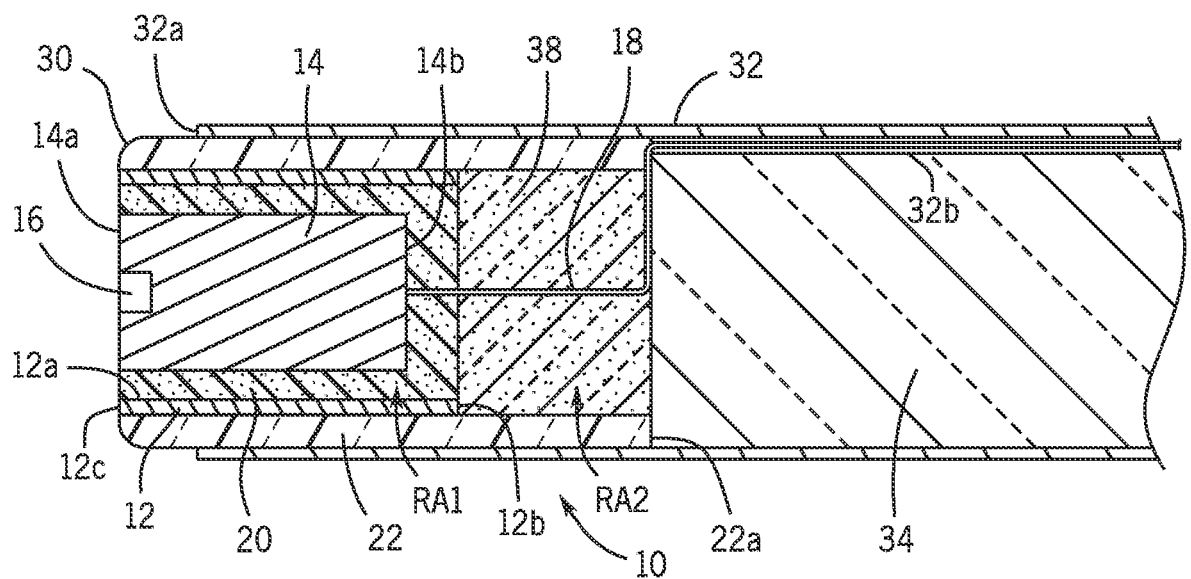
FIG. 2 is an axial cross-section of the micro-endoscope of FIG. 1 taken along the line 2-2 of FIG. 1.

With additional reference to FIGS. 2 and 3, the micro-endoscope 10 can include a mounting housing 12 and a camera module 14 (schematically illustrated) received within the mounting housing 12. As shown in the illustrated embodiment, the mounting housing 12 is in the form of, and is alternately referred to herein as, a mounting tube. By way of example, the camera module 14 can be a micro-CMOS camera module having optics 16 (e.g., camera lens) disposed on a forward facing imaging surface 14a of the camera module 14. A ribbon cable 18 (e.g., a bundle of wires carrying power and data) can be operatively connected to the camera module 14 at a rearward facing surface 14b of the camera module 14. For example, the ribbon cable 18 can be soldered to connections (not shown) provided on the rearward facing surface 14b. As used herein, the directional terms forward and rearward are relative to a distal end 10a of the micro-endoscope 10 such that forward facing is in a direction toward the distal end 10a and rearward facing is in a direction facing away from the distal end 10a.

The micro-endoscope 10 further includes an encapsulation material 20 and a light guide 22. The encapsulation material 20 is interposed between the camera module 14 and the mounting tube 12 for fixedly mounting the camera module 14 within the mounting tube 12 and/or inhibiting the passage of light between the camera module 14 and the mounting housing 12. The light guide 22 has the mounting housing 12 received or accommodated therein with the camera module 14 received within the mounting tube 12. In the illustrated embodiment, the light guide 22 is in the form of, and alternately referred to herein as, a light guide tube. The light guide tube 22 is annularly disposed around the mounting tube 12 for transmitting light axially past the camera module 14 and the mounting tube 12. In particular, glue or some other adhesive (not shown) can fixedly secure the mounting tube 12 and the light guide 22 together. In one embodiment, the light guide 22 can be formed of a light transmissive plastic.

Advantageously, the encapsulation material 20 and the inclusion of the mounting tube 12 overcome many of the drawbacks of known micro-endoscopes. In particular, providing the camera module 14 in an encapsulated state within the mounting tube 12 allows for good installation of the mounting tube 12 into the light guide 22. More specifically, the outer dimensions of the mounting tube 12 can be more precisely controlled than those of the camera module and/or the camera module with black paint added thereon. This enables a repeatable interference fit between the mounting tube 12 and the guide tube 22 that often failed in the known arrangement. Additionally, the use of the encapsulation material 20 instead of paint enables filling of any gaps between the camera module 14 and the surrounding mounting tube 12 and light guide 22. In contrast with the known arrangement that used paint, the use of the encapsulation material 20 better inhibits or reduces stray light from passing between the light and the camera (i.e., instead, light can only pass physically through the light guide). Further, adherence of the encapsulation material 20 is much greater than paint so the problem with parasitic paint particles is greatly reduced or eliminated.

The camera module 14 of the illustrated embodiment includes the forward facing imaging surface 14a and lateral walls 14c orthogonally extending rearwardly from the forward facing imaging surface 14a. The encapsulation material 20 is interposed between the lateral walls 14c and an inner radial surface 12a of the mounting tube 12. More particularly, the camera module 14 of the illustrated embodiment is generally cuboid shaped, though this is not required, and includes the rearward facing surface 14b opposite and spaced apart from the forward facing imaging surface 14a with the lateral walls 14c extending therebetween. The camera module 14 is arranged so as to form, at least in part, the distal end 10a of the micro-endoscope 10.

As shown, the encapsulation material 20 fully surrounds the camera module 14 and fills any gap between the camera module 14 and an interior (i.e., the inner radial surface 12a) of the mounting tube 12. The rearward facing surface 14b is axially spaced apart from a rear axial end 12b of the mounting tube 12 to define a first rearward area RA1 axially rearwardly of the rearward facing surface 14b. The encapsulation material 20 also fills the area RA2 so the encapsulation material 20 is disposed axially between the rearward facing surface 14b of the camera module 14 and the rear axial end 12b of the mounting tube 12 to fully encapsulate the rearward facing surface 14b of the camera module 14. Additionally, the encapsulation material 20 in this area secures the connection of the ribbon cable 18 to the camera module 14.

More specifically, the ribbon cable 18 is electrically connected to the camera module 14 (e.g., via soldered connections, not shown). In an known micro-endoscope, the soldered connections between a ribbon cable and the associated camera module are susceptible to failure. In the exemplary embodiment described and illustrated herein, encapsulation via the encapsulation material 20 enhances the connection of the ribbon cable 18 to the camera module 14 to inhibit inadvertent breakage or failure of the soldered connection between the ribbon cable 18 and the camera module 14. In an exemplary embodiment, the encapsulation material both fixedly mounts the camera module 14 within the mounting tube 12 and inhibits light transmission between the camera module 14 and the mounting tube 12. This arrangement also provides extra rigidity to the ribbon cable 18 by causing any force transmitted at that location to be imparted into the encapsulation material 20 instead of being handled by soldered connections between the ribbon cable 18 and the camera module 14. This provides increased mechanical robustness for the micro-endoscope 10 because strain relief for the ribbon cable 18 is provided.

In one exemplary embodiment, the encapsulation material 20 can be an adhesive that is optically black. Additionally, the encapsulation material 20 can be bio-compatible. For example, the encapsulation material 20 can be formulated to meet USP Class VI and ISO 10993 standards for use in the body. Additionally, or in the alternative, the encapsulation material 20 can be formulated such that it is stable against a wide variety of chemicals normally found in medical settings. In one specific exemplary embodiment, the encapsulation material 20 can be formed as a mixture of a two component epoxy adhesive and a colorant. One such exemplary two component epoxy has a specific gravity of about 1.16, a viscosity of about 30 Pas at 25 degrees Celsius, a cure time of about 5 hours to reach more than 10 Mpa of lap shear strength and about 23 hours to reach more than 1 MPa of lap shear strength. The epoxy can be transparent/color free and solvent free. A specific exemplary two component epoxy is sold under the trade name ARALDITE® CRYSTAL by Huntsman Advanced Materials (of Switzerland). The colorant can be a concentrated black colorant or pigment. A specific exemplary colorant is sold under the trade name EPO-TEK #11 by Epoxy Technology, Inc. (of Billerica, Mass.). An exemplary mixture ratio is 5-7% by weight of the colorant is added to the two-part epoxy. Alternately, another exemplary encapsulation material is an optically black adhesive (no colorant needed). a specific exemplary such adhesive is sold under the trade name EPO-TEK 320-3M by Epoxy Technology, Inc. (of Billerica, Mass.).

In the same or another exemplary embodiment, the mounting tube 12 can be selected from a thin material (e.g., a metallic material) that is not light transmissive and/or has a high reflectivity across the visible spectrum. For example, the mounting tube 12 can be formed from a material that has a light reflectivity greater than about 80%. Additionally, or in the alternative, the mounting tube can be selected from a material that has high ductility. By way of a specific example, the mounting tube 12 can be formed of a very thin (e.g., about 59 μm) aluminum or an aluminum alloy for preventing light transmission therethrough and providing high reflectivity across the visible spectrum (e.g., greater than 80%) to increase light transmission through the light guide tube 22.

As best shown in FIG. 2, a rearward axial end 22*a* of the light guide tube 22 can be axially spaced apart from the rear axial end 12*b* of the mounting tube 12 to form a second rearward area RA2. Accordingly, the rearward axial end 22*a* of light guide tube 22 is also axially spaced apart from the rearward facing surface 14*b* of the camera module 14. An adhesive 38 can fill the area RA2 radially within the light guide tube 22 adjacent or at the rearward axial end 22*a*, and axially rearward of the mounting tube 12 and the encapsulation material 20 disposed therein. The adhesive 38 can be a clear or light transmissive adhesive, such as an optically clear epoxy. In one exemplary embodiment, the adhesive 38 can use the same epoxy used to mix with a colorant to form the encapsulation material described above. As a specific example, the adhesive 38 could be a two component epoxy such as the one sold under the trade name ARALDITE® CRYSTAL by Huntsman Advanced Materials (of Switzerland). Alternatively, the adhesive 38 could be a reflective epoxy. For example, a reflective epoxy can be optically clear but with the inclusion of light scattering particles, such as metallic flakes. In one exemplary example, the light scattering particles can be aluminum or formed form another material with a reflective coating thereon.

As also shown and mentioned above, the forward facing imaging surface 14*a* of the camera module 14 and a forward axial end 12*c* of the mounting tube form the distal end 10*a* of the micro-endoscope 10. Additionally, the light guide tube 22 has a forward axial end 22*b* axially aligned with the forward facing imaging surface 14*a* of the camera module 14 and the forward axial end 12*c* of the mounting tube 12. Thus, the light guide tube 22, and particularly the forward axial end 22*b* thereof, also forms the distal end 10*a* of the micro-endoscope. As shown in the illustrated embodiment, the forward axial end 22*b* of the light guide 22 can include a chamfered edge 30 (see FIG. 1) for controlling light distribution as is known and understood by those skilled in the art. In one embodiment, the chamfered edge 30 is formed using a hand miller with a curved attachment and/or has a convex arc between 60 and 90 degrees.

The micro-endoscope 10 can additionally include a tubular scope shaft 32 annularly disposed around the light guide 22. In particular, a forward axial end 32*a* of the tubular scope shaft 32 can be axially spaced apart rearwardly from the forward facing imaging surface 14*a* of the camera module 14 and from the forward axial end 12*c* of the mounting tube 12. By way of example, the tubular scope shaft 32 can be formed of a metal, such as stainless steel. Still further, the micro-endoscope 10 can include an optical fiber 34 abutting the rearward axial end 22*a* of the light guide tube 22 and housed within the tubular scope shaft 32. The adhesive 38 can optionally fixedly secure the optical fiber 34 to the light guide 22.

With additional reference to FIG. 4, the mounting tube 12 can include an axial slit 26 for increasing dimensional tolerance of the camera module 14. In particular, the axial slit 26 can provide some dimensional flexibility for the mounting tube 12 thus enabling adjustment of its diameter. More specifically, the axial slit 26 acts as a tolerance compensator (i.e., spring effect) and ensures a good fitting of the camera module 14. Accordingly, the mounting tube 12 can better accommodate camera modules that are dimensionally out of spec so insertion into the light guide tube 22 and the tubular scope shaft 32 is more repeatable, with camera positioning being more consistent.

With reference to FIG. 5, the light guide tube 22 includes or defines a notch 36 for accommodating the ribbon cable 18. In particular, in the illustrated embodiment, the ribbon cable 18 extends from the rearward facing surface 14*b* of the camera module 14 and then extends axially at or near an axial centerline of the micro-endoscope 10 until reaching about the rearward axial end 22*a* of the light guide tube 22. At this location, the ribbon cable 18 makes a ninety degree turn and passes through the notch 36 before entering an axial recess 32*b* defined radially into an circumferential surface of the optical fiber 34 and defined along an axial extent of the optical fiber 34.

With reference to FIG. 6, another light guide tube 22' is shown according to an alternate embodiment. The light guide tube 22' of FIG. 6 can replace the light guide tube 22 in the embodiment shown in FIGS. 1-5, though the tubular shaft 32 would be modified to accommodate the non-linear shape of the light guide 22'. Advantageously, the rearward axial end 22*a'* of the light guide tube 22' is closed and has a tapered interior that narrows in a rearward direction away from the camera module 14 to define a conical chamber 40. This allows less clear adhesive 38 to be used and increases the amount of light transferred through the light guide tube 22'. In all other aspects, the light guide tube 22' can be used and arranged in the same manner as the light guide tube 22.

Figure 7:
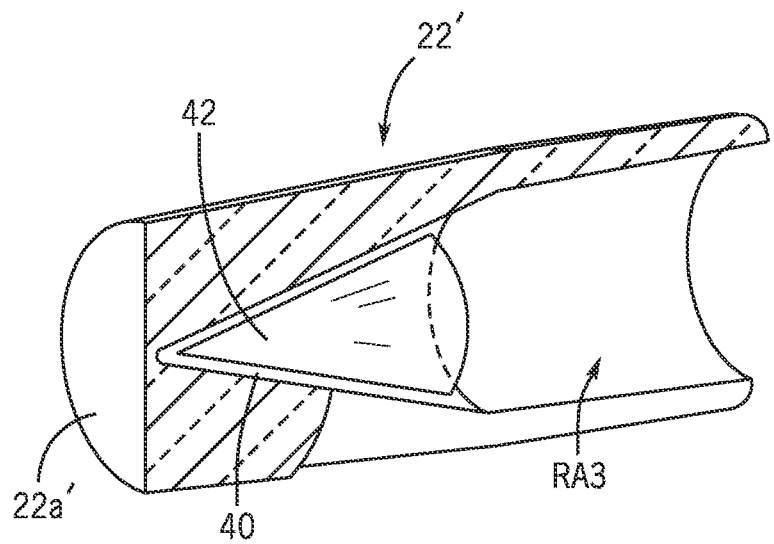
FIG. 7 is a perspective view similar to FIG. 6 but showing a cone complementarily received within the light guide tube according to a further alternate exemplary embodiment.
Figure 8:
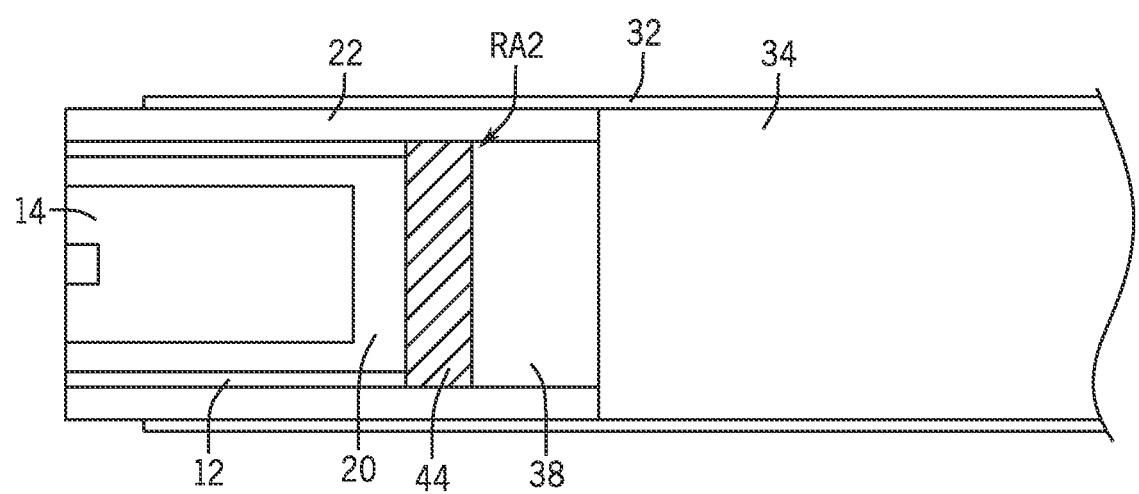
FIG. 8 is a schematic cross-section view similar to FIG. 2 but shown schematically and shown including a disc or puck shaped member according to an exemplary embodiment.

With additional reference to FIG. 7, the light guide 22' can optionally be used with a cone 42 received complementarily within the conical chamber 40 for absorbing heat coming from the camera module 14 (e.g., via heat transfer through the encapsulation material 20 and/or through the mounting tube 12) and/or for reflecting light away from the camera module 14 and/or the encapsulation material 20 surrounding the camera module 14. In one embodiment, the cone 42 is formed of a material (e.g., a metal, such as aluminum) having good heat conducting properties. In addition, or in the alternative, the cone 42 can be formed from, or coated with, a material having high light reflectivity (e.g., greater than about 80%). In one embodiment, the cone 42 is formed as a metallic object, optionally with a reflective coating, so as to absorb heat from the camera module 14 and to reflect light radially away from the camera module 14. When absorbing heat, the temperature at the distal end 10*a* of the micro-endoscope 10 is reduced. When the cone 42 is included within the light guide 22', the adhesive 38 can be accommodated within the light guide 22' axially rearward of the cone 42 in area RA3. Though not shown, a light reflecting and/or heat absorbing member (e.g., disc or puck shaped member 44 of FIG. 8) could be used in the embodiment shown in FIG. 2 that functions the same or similar to the cone 42 of FIG. 7. For example, with reference to FIG. 8, disc or puck shaped member 44 could be axially adjacent the encapsulation material 20 in the area RA2 while leaving an axial rearward portion of the area RA2 available for receiving the adhesive 38. The disc or puck shaped member 44 could absorb heat coming from the camera module 14 (e.g., via heat transfer through the encapsulation material 20 and/or through the mounting tube 12) and/or reflect light away from the camera module 14 and/or the encapsulation material 20 surrounding the camera module 14.

Instead of the cone 42, a high thermal conductivity material (e.g., a thermal gel) could be used in the light guide 22' or, instead of the disc or puck shaped member 44, a high thermal conductivity material could be used in the light guide 22 in FIG. 2. The high thermal conductivity material could also be used to replace some amount of the adhesive 38 in the light guide 22' of FIG. 7 or in the light guide 22 of FIG. 2. The high thermal conductivity material could be used to absorb heat from the camera module 14 (e.g., in the same manner that the cone 42 absorbs heat). In one embodiment, the high thermal conductivity material could be a gel or semi-gel that dissipates heat from the camera module 14. The high thermal conductivity material could function in the same manner as the cone 42 or the member 44 to absorb heat and reduce the temperature at the distal end 10a of the micro-endoscope 10. In an exemplary embodiment, the high thermal conductivity material has a thermal conductivity that is about 10 times greater than a light polycarbonate, such as for example a thermal conductivity of about 1 W/m-K. The adhesive 38 would be added axially rearward of the high thermal conductivity material to seal in the material within the light guide 22 or 22'. For example, referring to FIG. 8, the high thermal conductivity material could replace the member 44 and would be sealed within the light guide 22 by the adhesive 38.

Figure 9:
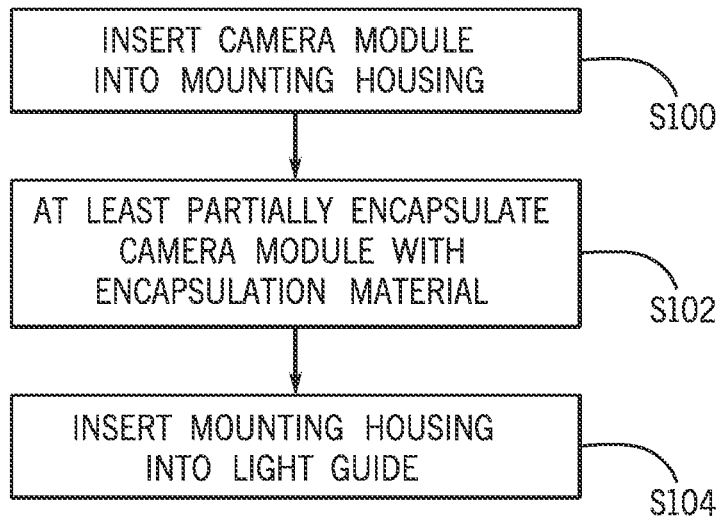
FIG. 9 is a process flow diagram illustrating a method of making a micro-endoscope according to an exemplary embodiment.

With reference now to FIG. 9, a method of making a micro-endoscope will be described. In particular, the method of FIG. 9 will be described in association with the micro-endoscopes discussed hereinabove, though this is not required and it is to be appreciated that the method can be used with other micro-endoscopes. In the method, at S100, the camera module 14 is inserted into the mounting housing 12. At S102, the camera module 14 is at least partially encapsulated with the encapsulation material 20 interposed between the camera module 14 and the mounting housing 12 for fixedly mounting the camera module 14 within the mounting housing 12 and/or inhibiting the passage of light between the camera module 14 and the mounting housing 12.

In one embodiment, the encapsulation material 20 is inserted inside the mounting housing 12, such as via an applicator with a fine tip. Optionally, heat can be applied, such as by a heat gun, to decrease the viscosity of the encapsulation material 20 and ensure that the encapsulation material 20 fills in all gaps around the camera module 14. With the camera module 14 fully installed or inserted into the mounting housing 12, further encapsulation material 20 can be injected into or added to the mounting housing 12 so that the rear facing surface 14b of the camera module 14 is fully encapsulated and the ribbon cable 18 is fully encapsulated particularly where the ribbon cable 18 connects to the camera module 14. As already mentioned herein, the encapsulation material 20 can be selected so that the material functions to both fix the camera module 14 within the mounting housing 12 and blocks the transmission of light thereby so that no light can pass between the camera module 14 and the inner radial surface 12a of the mounting housing 12.

Next, at S104, the mounting housing 12, with the camera module 14 already inserted therein, can be itself inserted into the light guide 22 (or into the light guide 22'). This can include the application of a glue or other adhesive to fix the mounting housing to the light guide 22 or 22'. The method could end after S104 such as in the case where the subassembly including the mounting housing 12, the camera module 14 and the light guide 22 is to be shipped remotely before being fully assembled into the micro-endoscope 10.

Figure 10:
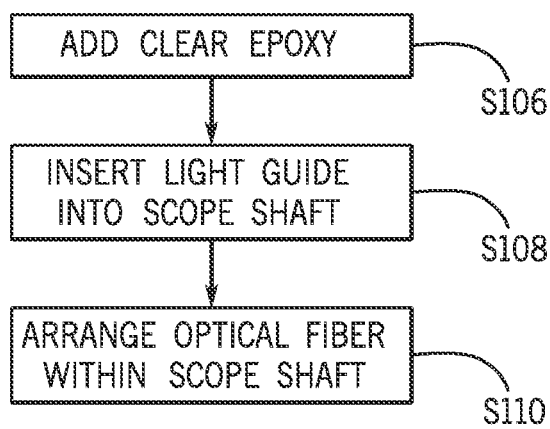
FIG. 10 is a further process flow diagram further illustrating a method of making a micro-endoscope according to an exemplary embodiment.

In the alternative, with additional reference to FIG. 10, the method can continue at 106. In particular, after the mounting housing 12 is inserted into the light guide 22 22' in S104, the adhesive 38 can be added at S106 within the light guide 22 or 22' rearward of the camera module 14, mounting housing 12, and encapsulation material 20. Then, at S108, the light guide 22 or 22' can be inserted into the tubular scope shaft 32 and, at S110, the optical fiber 34 can be arranged within the tubular scope shaft 32 in abutting contact with the rearward axial end 22a of the light guide 22 (or light guide 22').

Before or after steps S106, S108 and S110, the light guide 22 (or light guide 22'), and particularly the forward axial end 22b thereof, can be chamfered, as is known and understood by those skilled in the art, so as to provide chamfered edge 30 (FIG. 1) on the light guide for controlling light distribution. As indicated above, in one embodiment, the chamfered edge 30 is formed using a hand miller with a curved attachment and/or has a convex arc between 60 and 90 degrees. The chamfering step can include the removal of any excess encapsulation material 20 from the camera module. In addition, or in the alternative, cleaning of the camera module 14 can occur at any time (and multiple times) before or between steps S100-S110. In one embodiment, the camera module 14 is cleaned using isopropyl alcohol and a cotton swab to remove any residues (e.g., encapsulation material 20 flowing onto the camera module 14).

Optionally, a light reflecting and/or heat absorbing member, such as cone 42 or member 44 can be installed in the appropriate light guide 22' or 22 prior to the adhesive 38 being added. Alternatively, a high thermal conductivity material could be used instead of the cone or member 44.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An endoscope, comprising:
   a scope shaft, having an outer surface, and an inner surface;
   a camera module inside the scope shaft at a first end of the scope shaft, and having a light receiving surface imaging an area at the first end of the scope shaft;
   a light guide, having a light receiving end, receiving light for illuminating the area at the first end of the scope shaft, the light guide transmitting the light along the light guide from the light receiving end to the area at the first end of the scope shaft;
   wherein the light guide surrounds an inside area which is inside the light guide and defines a conical chamber; and
   a cone shaped heat conducting structure, the cone shaped heat conducting structure having a point at one end, and having a flat second end, and the cone shaped heat conducting structure conical in shape structure received complimentarily within the conical chamber on the inside area of the light guide at a location between the light receiving end and the camera module, and the cone shaped heat conducting structure located to and operative to absorb heat.

2. The endoscope as in claim 1, wherein the heat conducting structure is a solid cone which is glued in place using an adhesive.

3. The endoscope as in claim 1, wherein a section of the light guide changes progressively in thickness, forming the conical section.

4. The endoscope as in claim 1, further comprising an optical fiber, supplying light to an optical receiving end of the light guide.

5. The endoscope as in claim 1, wherein the heat conducting structure absorbs heat from the camera module.

6. An endoscope, comprising:
- a scope shaft, having an outer surface, and an inner surface;
- a camera module inside the scope shaft at a first end of the scope shaft, and having a light receiving surface imaging an area at the first end of the scope shaft;
- a light guide, having a light receiving end, receiving light for illuminating the area at the first end of the scope shaft, the light guide transmitting the light along the light guide from the light receiving end to the area at the first end of the scope shaft;
- wherein the light guide surrounds an inside area which is inside the light guide;
- wherein a first section of the light guide changes progressively in thickness, forming a conical section, at the first section; and
- wherein a second section of the light guide has a constant thickness;
- a cone shaped heat conducting structure, the cone shaped structure having a point at one end, and having a flat second end, the cone shaped structure being received complimentarily within the conical chamber on the inside of the first section of the light guide and operative to absorb heat from the camera module.

7. The endoscope as in claim 6, wherein the heat conducting structure is a solid cone which is glued in place using an adhesive.

* * * * *